United States Patent [19]

Piccardi et al.

[11] 4,126,623

[45] Nov. 21, 1978

[54] BENZYL OR PHENYL ETHERS AND THIOETHERS WITH A LINEAR ALIPHATIC CHAIN HAVING A HALOGENATED END GROUP AND EXHIBITING JUVENILE HORMONE AND ACARICIDE ACTIVITY

[75] Inventors: Paolo Piccardi; Pietro Massardo; Angelo Longoni, all of Milan, Italy

[73] Assignee: Montedison S.p.A., Milan, Italy

[21] Appl. No.: 787,491

[22] Filed: Apr. 14, 1977

[30] Foreign Application Priority Data

Apr. 15, 1976 [IT] Italy .................................. 22349 A/76

[51] Int. Cl.$^2$ ........................................... C07D 317/44
[52] U.S. Cl. ........................... 260/340.5 R; 260/609 E; 424/282; 424/337; 424/340; 568/656; 568/655; 568/649; 568/663; 568/588
[58] Field of Search .................. 260/340.5 R; 424/282

[56] References Cited

U.S. PATENT DOCUMENTS

| 3,423,428 | 1/1969 | Fellig et al. ........................ 260/340.5 |
| 3,524,915 | 8/1970 | Fellig et al. ........................... 424/282 |
| 3,796,726 | 3/1974 | Edwards ........................... 260/340.5 |
| 3,933,804 | 1/1976 | Scheling et al. .............. 260/340.5 X |
| 3,941,884 | 3/1976 | Edwards ............................. 424/282 |
| 3,968,235 | 7/1976 | Schelling et al. .................... 424/282 |

Primary Examiner—Ethel G. Love

[57] ABSTRACT

There are disclosed ethers and thioethers having a benzyl or phenyl terminal group and another terminal group which is halogenated, and which ethers and thioethers exhibit juvenile hormone activity (i.e., function as inhibitors of the development of insects from their larval state to the adult state), as well as acaricide activity.

Methods for preparing the ethers and thioethers are also disclosed.

4 Claims, No Drawings

BENZYL OR PHENYL ETHERS AND THIOETHERS WITH A LINEAR ALIPHATIC CHAIN HAVING A HALOGENATED END GROUP AND EXHIBITING JUVENILE HORMONE AND ACARICIDE ACTIVITY

THE PRIOR ART

Italian application No. 19,332 A/74 and in addition thereto, No. 28583 A/74, both assigned to Montedison, S.p.A., and corresponding to Piccardi et al U.S. Pat. No. 4,000,312, issued Dec. 28, 1976, disclosed unsaturated aliphatic compounds having a vinyl dichloro and trichloro-substituted terminal group, and which exhibit juvenile hormone activity. A later Italian application, No. 28116 A/75, also assigned to Montedison S.p.A., and corresponding to U.S. application Ser. No. 731,047 filed Oct. 8, 1976, disclosed unsaturated aliphatic compounds having a terminal chloromethyl group and a terminal phenyl or substituted phenyl group, and which exhibit both juvenile hormone and acaricide activity.

The compounds of said Italian applications, due to various unsaturations and to methyl or ethyl side groups can be considered as having a terpenoid activity.

THE PRESENT INVENTION

An object of this invention was to provide new compounds having both juvenile hormone and acaricide activity.

This and other objects are achieved in accordance with the present invention which provides ethers and thioethers having a benzyl or phenyl terminal group and another terminal group which is halogenated, and which correspond to the following general formula:

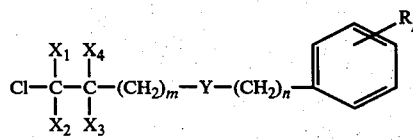

wherein:
$X_1$ = H; F; Cl, or together with $X_2$, $X_3$ and $X_4$ represent a trifold bond C—C;
$X_2$ = Cl, or, when $X_1$ is different from Cl, represent, together with $X_3$ or $X_4$, a double C—C bond; or with $X_1$, $X_3$ and $X_4$ a trifold C—C bond;
$X_3$ = H; Cl, or, when $X_1$ is different from Cl, forms, together with $X_2$, a double C—C bond; or with $X_1$, $X_2$ and $X_4$ a trifold C—C bond;
$X_4$ = H; or when $X_1$ is different from Cl, forms together with $X_2$ a double C—C bond; or together with $X_1$ or $X_2$ and $X_3$ forms a trifold C—C bond;
H = O; S;
$m$ = 3, 5, 7;
$n$ = 0, 1;
$p$ = a whole number from 1 to 4;
R = $C_1$-$C_5$ alkoxy, allyloxy, propargyloxy, 3,4-dioxymethylene, dichloro-allyloxy, halogen, $C_1$-$C_5$-alkyl, $C_2$-$C_5$-alkenyl or chloroalkenyl, propargyl, $C_1$-$C_5$-alkylcarbonyl, $C_1$-$C_5$-alkylcarboxyl, $C_1$-$C_5$-alkylcarbamoyl, $C_1$-$C_5$-alkylthio, $C_2$-$C_5$-alkenylthio nitro- or cyano- groups having both juvenile hormone as well as acaricide activity.

The new ethers and thioethers of formula (I) are prepared by reacting a compound of the general formula

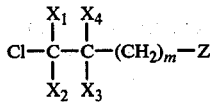

wherein:
$X_1$, $X_2$, $X_3$, $X_4$ and m have the same meaning as in formula (I), while Z represents a Cl, Br or an I atom, with a compound of the general formula:

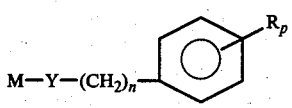

wherein:
R, Y, $n$ and $p$ have the same meaning as in formula (I) and M represents an alkaline metal or ammonium.

The starting compounds of general formula (II) are known only in part. They are prepared by reacting a halogenated methane of the general formula:

$$CCl_2X_1-Z \qquad (IV)$$

wherein:
$X_1$ and Z have the same meaning as in formula (II), with ethylene, using catalysts of the type described by M. Ascher and D. Vofsi in JCS, 1963, 1887, or with initiators of the peroxide type, for instance of the type described by Kharasch et al in JACS 67, 1626 (1945).

In this way there are obtained telomeric mixtures from which, by fractional distillation, there are obtained compounds of general formula:

$$CCl_2X_1-CH_2(CH_2)_m-Z \qquad (V)$$

wherein $X_1$, Z and m have the meaning as in formula (II).

The compounds of formula (V) can be further processed to obtain compounds of general formula (II) by:
(a) dehydrochlorination to compounds of the general formula:

$$CClX_1 = CH-(CH_2)_m-Z \qquad (VI)$$

wherein $X_1$, Z and $m$ have the same meaning as in formula (II);
(b) chlorination of the compounds of formula (VI) to substances of the general formula:

$$CCl_2X_1-CHCl-(CH_2)_m-Z \qquad (VII)$$

wherein $X_1$, Z and $m$ have the same meaning as in general formula (II);
(c) dehydrochlorination of the compounds of general formula (VII) to compounds of the general formula:

$$CClX_1 = CCl-(CH_2)_m-Z \qquad (VIII)$$

wherein $X_1$, Z and $m$ have the same meaning as in general formula (II).

When operating with halogenated methane of the type $CCl_3$—Z it is possible to obtain, as described in the preparation of compounds (V), products of the general formula:

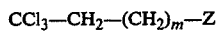  (IX)

wherein Z and m have the same meaning as in formula (II), and which may be twice dehydrochlorinated in order to give compounds of general formula:

  (X)

wherein m and Z have the same meaning as in formula (II).

The general formulae: (V), (VI), (VII), (VIII) and (X) can be summarized by general formula (II).

The ethers or thioethers of general formula (I) differ from the compounds disclosed in the aforementioned Italian applications in not having a terpenoid structure. Since the ethers and thioethers of this invention do not contain a double or trifold bond in the aliphatic chain they have a high degree of stability in the open air and in the soil. They are endowed with a considerable juvenile hormonic activity and an acaricide activity, as shown in Example 16, infra.

While all ethers and thioethers of the invention exhibit good juvenile hormone activity on the pupae of Tenebrio molitor, these new ethers and thioethers show a certain selectivity, some being active with respect to particular insect species, others being active with respect to other and different species of insect. In general, the acaricide activity is more pronounced on the eggs of Tetranychus urticae, although very often even the adults prove to be sensitive.

Particularly effective and useful ethers and thioethers of the invention are the following; characteristics given were determined from the nuclear magnetic resonance spectra:

1-(5-chloro-5-fluoro-pent-4-enyl-oxy)-4-chlorobenzene of formula:

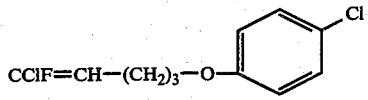

(our mark JH88), having the following characteristics: $^1$H NMR (CDCl$_3$) δ = 1, 4–2 (2H multiplet complex), 2–2.5 (2H multiplet complex), 3.95 (2H triplet), 4.45–5.45 (1H multiplet complex), 6.95 (4H);

5-chloro-5-fluoro-pent-4-enyl-benzyl sulphide of formula:

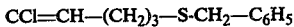

(our mark JH89) having the following characteristics: $^1$H NMR (CDCl$_3$) δ = 1.35–2.45 (6H, multiplet), 3.65 (2H, singlet), 4.45–5.45 (1H, m.), 7.25 (5H, s.);

1-(5-chloro-pent-4-inyl-oxy)-4-chlorobenzene of formula:

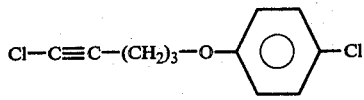

(our mark IH92) having the following characteristics: $^1$H NMR (CDCl$_3$) δ = 1.65–2.45 (4H multiplet complex), 3.9 (2H, triplet), 6.94 (4H).

1-(7-chloro-ept-6-inyl-oxy)-4-chlorobenzene of formula:

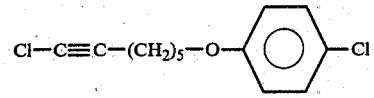

(our mark JH93) having the following characteristics: $^1$H NMR (CDCl$_3$) δ = 1.3–2 (6H complex), 2.2(2H, triplet), 3.85 (2H, triplet), 6.95 (4H);

7-chloro-7-fluoro-ept-6-enyl-benzyl sulphide of formula:

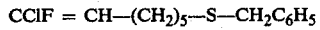

(our mark JH107) having the following characteristics: $^1$H NMR (CDCl$_3$) δ = 1.2–1.8 (6H complex), 1.9–2.3) (2H, m. complex), 2.4 (2H, t), 3.7 (2H s), 4.45–5.45 (1H m.compl.), 7.25 (5H, singlet).

1-(7-chloro-hept-6-inyl-oxy)-4-ethylbenzene of formula:

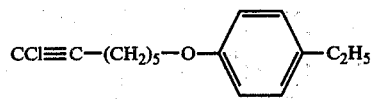

(our mark JH108) having the following characteristics: $^1$H NMR (CDCl$_3$) δ = 1.22 (3H, triplet), 1.35–2 (6H,m. complex), 2.22 (2H, t), 2.6(2H, q), 3.96 (2H, f), 7.0 (4H).

1-(7-chloro-ept-6-inyl-oxy)-3,4-methylendioxybenzene of formula:

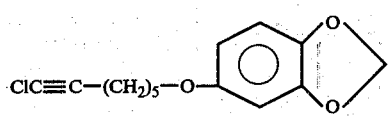

(our mark JH109, having the following characteristics: $^1$H NMR (CDCl$_3$) δ = 1.4–1.9 (6H, complex), 2.2 (2H, t), 3.9 (2H, t), 5.9 (2H, s), 6.2–6.9 (3H, complex).

1-(7,7-dichloro-7-fluoro-heptyl-oxy)3,4-methylendioxybenzene of formula:

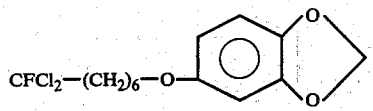

(our mark JH96) having the following characteristics: m.p. 25°–27° C, $^1$H NMR (CDCl$_2$) δ = 1.3–2.1 (8H, complex) 2.1–2.8 (2H, complex), 3.85 (2H, t), 5.8 (2H, s), 6.15–6.7 (3H, m).

1-(7,7-dichloro-7-fluoro-heptyl-oxy)-4-methoxy-benzene of formula:

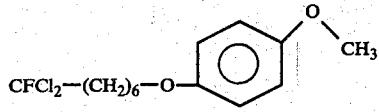

(our mark JH97) having the following characteristics: m.p. 43° C, $^1$H NMR (CCl$_4$) δ = 1.3–2.1 (8H, complex) 2.1 to 2.8 (2H, complex), 3.8 (3H, s), 3.92 (2H, t), 6.84 (4H, s).

5-chloro-5-fluoro-pent-4-enyl-benzylether of formula:

$CFCl=CH-(CH_2)_3-O-CH_2-C_6H_5$ (our mark JH98) having the following characteristics:
$^1H$ NMR (CDCl$_3$) δ = 1.4–1.9 (2H, m. complex), 1.95–2.4 (2H, m. complex), 3.42 (2H, t), 4.42 (2H, s), 4.45–5.45 (1H, m. complex), 7.25 (5H, s).

1-(7-chloro-7-fluoro-hept-6-enyl-oxy)-4-methoxybenzene of formula:

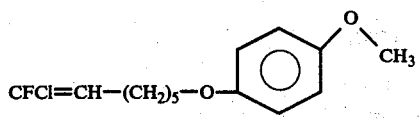

(our mark JH99) having the following characteristics:
$^1H$ NMR (CDCl$_3$) δ = 1.3–2.2 (8H, complex), 3.7 (3H, s), 3.85 (2H, t), 4.5–5.4 (1H, complex), 6.80 (4H, s).

1-(7-chloro-7-fluoro-hept-6-enyl-oxy)-3,4-methylendioxybenzene of formula:

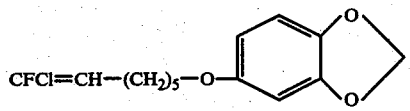

(our mark JH100) having the following characteristics:
$^1H$ NMR (CDCl$_3$) δ = 1.2–2.3 (8H, complex), 3.85 (2H, t), 4.5–5.4 (1H, complex, 5.8 (2H, s), 6.1–6.8 (3H, multiplet).

1-(7-chloro-7-fluoro-hept-6-enyl-oxy)-4-chlorobenzene of formula:

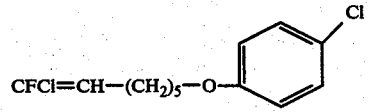

(our mark JH101) having the following characteristics:
$^1H$ NMR (CDCl$_3$) δ = 1.2–2.25 (8H, not resolved), 3.9 (2H, t), 4.45–5.45 (1H, m. complex), 6.96 (4H).

The ethers and thioethers of the invention can be formulated in different ways, for instance they can be absorbed, in quantities of from 0.5 to 50% or more on powders according to known methods. They may also be used in the form of emulsions or aqueous suspensions, using known surfactants. Moreover they may be spread in the form of solutions in suitable solvents such as alcohol, acetone, etc.

The ethers and thioethers as such, or suitably formulated, may be spread over the habitat of the adult insects to be destroyed, or they may be introduced into their food, or spread over the habitat and over the food of their larvae and pupae (chrysalides) or on their eggs, in quantities of at least 0.2 parts per million.

The following examples are given to illustrate the invention in more detail and are not intended to be limiting.

EXAMPLE 1

Preparation of CCl$_3$-(CH$_2$)$_m$CH$_2$Cl intermediates; m = 3, 5, 7.

The process described by M Ascher et al in "*Industrial and Engineering Chemistry (Product Research and Development)*" Vol. 2, No. 2, 121, 1963 was used and the intermediates were recovered by fractional distillation:

| | |
|---|---|
| 1,1,1,5-tetrachloro-pentane | 70° – 72° C at 2 mm/Hg |
| 1,1,1,7-tetrachloro-heptane | 92° – 94° C at 2 mm/Hg |
| 1,1,1,9-tetrachloro-nonane | 120° – 122° C at 2 mm/Hg |

EXAMPLE 2

Preparation of CHCl$_2$—(CH$_2$)$_m$CH$_2$Cl intermediates; m = 2, 5, and 7.

CHCl$_2$ and ethylene were reacted using catalysts, solvents and procedures as described by M. Ascher and D. Vofsi in JCS, 1963, 3927, and the intermediates were recovered by fractional distillation:

| | |
|---|---|
| 1,1,5-trichloropentane | b.p. 84° – 86° C at 9 mm/Hg |
| 1,1,7-trichloroheptane | b.p. 73° C at 1 mm/Hg |
| 1,1,9-trichloro-nonane | b.p. 123° C at 3 mm/Hg |

EXAMPLE 3

Preparation of CFCl$_2$—(CH$_2$)$_m$—CH$_2$Cl intermediates; m = 3, 5, 7.

Into a stainless steel, 2 lt autoclave were introduced 600 ml of CFCl$_3$, 1.5 ml of ter-butyl-peroxide and ethylene up to saturation at a temperature of 30° C.

The reaction mixture was then heated under stirring up to 140° C, at which temperature the inside pressure of the autoclave was brought up to 45 atm by the continuous introduction of ethylene. After 5 hours, the autoclave was cooled down and the content was recovered. By fractional distillation of the liquids there were obtained:

| | |
|---|---|
| 50 g 1,1,5-trichloro-1-fluoropentane | b.p. 78° /15 mm/Hg |
| 40 g 1,1,7-trichloro-1-fluoroheptane | b.p. 65° /1 mm/Hg |
| 15 g 1,1,9-trichloro-1-fluorononane | b.p. 62° /0.1 mm/Hg |

EXAMPLE 4

Synthesis of 1-(6-dichlorofluoromethyl-hexyl-oxy)-4-methoxybenzene (JH97):

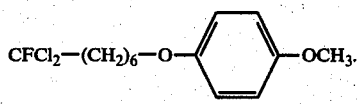

A mixture of 2,10 g of methoxyphenol, 2.3 g of K$_2$CO$_3$, 4.0 g of 1,1,7-trichloro-1-fluoroheptane (prepared as described in Example 3) and 50 ml of N,N-dimethylformamide was heated at 80° C for 16 hours, under stirring. At the end of this period, the reaction mixture was cooled down and then poured into 200 ml of H$_2$O. The organic phase and the etheric extracts of the aqueous phase were gathered together, dried and evaporated.

The raw product thus obtained was purified by chromatography in a silica column, using a 5% mixture of ethyl ether in hexane as eluent. Thereby, 1.3 g of 1-(6-dichlorofluoromethyl-hexyl-oxy)-4-methoxy-benzene having a m.p. of 43° C were obtained. $^1H$ NMR δ (CCl$_4$): 1.3–2.1 (8H, complex), 2.1–2.8 (2H complex), 3.8 (3H, s), 3.92 (2H, t), 6.84 (4H, s).

EXAMPLE 5

Synthesis of 1-(6-dichlorofluoromethyl-hexyl-oxy)-3,4-methylene-dioxybenzene (JH96):

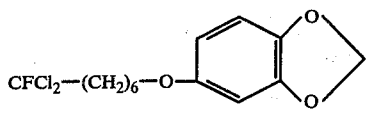

4.5 g of 3,4-methylenedioxyphenol, 3 g of $K_2CO_3$ and 3 g of 1,1,7-trichloro-1-fluoroheptane [prepared as described in Example (3)] were poured into 50 ml of N,N-dimethylformamide and kept under stirring for 24 hours at 50° C. Then, after leaving the mixture to rest overnight at room temperature, the reaction mixture was poured into water.

The organic phase and the etheric extracts of the aqueous phase were mixed together, washed, dried and evaporated. The raw product was then purified by chromatography in a column on silica, thereby obtaining 2 g of 1-(6-dichlorofluoromethyl-hexyl-oxy)-3,4-methylendioxybenzene, having a b.p. of 25°-27° C (from hexane).

$^1$H NMR $\delta$ (CDCl$_3$) = 1.3-2.1 (8H, complex), 2.1-2.8 (2H, complex), 3.85 (2H, t), 5.8 (2H, s), 6.15-6.7 (3H, multiplet).

EXAMPLE 6

Synthesis of 4-dichlorofluoromethyl-butyl-piperonyl ether (JH124):

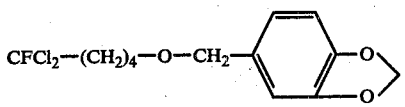

10 g of piperonyl alcohol (3,4-methylendioxy-benzyl-alcohol) were dissolved in 100 ml of 1,2-dimethoxyethane, and 3.2 g of NaH were added to the solution. The mixture was boiled for 30 minutes, after having been additioned with 16 g of 1,1,5-trichloro-1-fluoropentane [prepared as described in Example (3)] and with a I$_2$ crystal.

The heating was continued for 24 hours, after which the mixture was cooled down and then mixed with 150 ml of H$_2$O. Thereupon, there were admixed 150 ml of CH$_2$Cl$_2$ and the organic layer was separated, dried and evaporated. The raw product thus obtained was purified by chromatography in a silica column, using a 5% ethyl ether in hexane solution as eluent. Thereby were obtained 12 g of 4-dichloro-fluoromethyl-butyl-piperonyl ether, characterized by its NMR spectrum:

$^1$H NMR $\delta$ (CDCl$_3$) = 1.5-1.95 (4H, complex), 2.1-2.8 (2H, complex), 3.42 (2H, t), 4.4 (2H, s), 5.9 (2H, s), 6.8 (3H, complex). The elementary analysis showed: Theoretical Cl% = 23.8; found Cl% = 23.8.

EXAMPLE 7

Synthesis of 6-dichlorofluoromethyl-hexyl-piperonyl ether

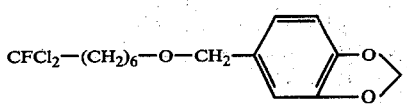

By operating as described in the preceding example, from 3 g of piperonyl alcohol and 4.5 g of 1,1,7-trichloro-1-fluoroheptane there were obtained 3.8 g of 6-dichloro-methyl-hexylpiperonyl ether, characterized by its NMR spectrum and elementary analysis.

EXAMPLE 8

Synthesis of 1-(7-chloro-7-fluoro-hept-6-enyl-oxy)-4-methoxybenzene (JH99):

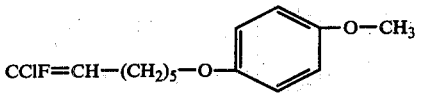

A — Preparation of 1,7-dichloro-1-fluoro-1-heptene 35.9 g of 1,1,7-trichloro-1-fluoroheptane were added to 32.5 ml of NaOH at 50% concentration and 0.65 g of triethylbenzylammonium chloride. Under vigorous stirring, the reaction mixture was heated at 100° C for 20 hours; it was then cooled down and extracted with ethyl ether. The ether solution was neutralized with diluted hydrochloric acid, repeatedly washed with water, dried and finally evaporated. From the distillation of the residue there were obtained 13.4 g of 1,7-dichloro-1-fluoro-1-heptene (1:1 mixture of cis- and trans- isomers) boiling at 40° C/0.2 mm Hg.

The product thus obtained showed a strong absorption band under IR spectroscopy at 1670 cm$^{-1}$ and the subsequent $^1$H NMR spectrum: $\delta$ (CDCl$_3$), 1.3-2.2 (8H, complex), 3.5 (2H, t), 4.5-5.4 (1H, multiplet complex).

B — Preparation of 1-(7-chloro-7-fluoro-hept-6-enyloxy)-4-methoxybenzene:

2.1 g of p-methoxyphenol were dissolved in 30 ml of N,N-dimethylformamide and were then additioned with 0.69 g of NaH (55% suspension in paraffin oil). The mixture was heated for 30 minutes at 50° C and then additioned with 3 g of 1,7-dichloro-1-fluoro-1-heptene. The heating was continued for 8 hours, under stirring. After a night at room temperature, the reaction mixture was poured into an equal volume of water. The organic phase and the ether extracts of the aqueous phase were gathered together, washed with water, dried and concentrated at reduced pressure.

The raw product thus obtained was purified by chromatography on silica in a column using as eluent an ether-hexane mixture with 5% ether. Thereby were obtained 2.5 g of 1-(7-chloro-7-fluoro-hept-6-enyl-oxy)-4-methoxybenzene, the $^1$H NMR spectrum of which showed the following readings: $\delta$ (CDCl$_3$): 1.3-2.2 (8H, complex), 3.7 (3H, s), 3.85 (2H, triplet), 4.5-5.4 (1H, complex), 6.80 (4H, singlet).

EXAMPLE 9

Synthesis of 1-(7-chloro-7-fluoro-hept-6-enyl-oxy)-3,4-methylendioxybenzene (JH100):

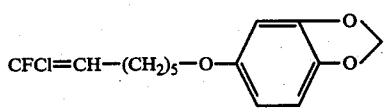

Operating as described in Example 8 (part B), from 3 g of 1,7-dichloro-1-fluoro-1-heptene, 2.14 g of 3,4-methylendioxyphenol, 0.69 g of NaH and 30 ml of N,N-dimethylformamide there were obtained 2.8 g of the product of the above-cited formula, a colorless oil.

$^1$H NMR δ (CDCl$_3$): 1.2–2.3 (8H complex), 3.85 (2H, t), 4.5–5.4 (1H, complex) 5.8 (2H, s), 6.1–6.8 (3H, multiplet).

EXAMPLE 10

Synthesis of 1-chloro-1-fluoro-5-benzylthio-pent-1-ene (JH89):

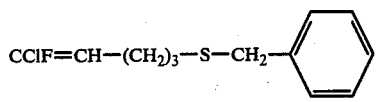

A — Preparation of 1,5-dichloro-1-fluoro-pent-1-ene.

Operating as described in Example 8 (part A), from 19.5 g of 1,1,5-trichloro-1-fluoropentane, 20 ml of NaOH at 50% concentration and 0.4 g of triethylbenzylammonium chloride were obtained 12.4 g of 1,5-dichloro-1-fluoropent-1-ene-, b.p. = 48° C/15 mm Hg.

B — Preparation of 1-chloro-1-fluoro-5-benzylthio-pent-1-ene 2.43 g of benzylmercaptan were mixed with 30 ml of N,N-dimethylformamide and then additioned with 0.7 g of NaH (55% in paraffin oil). Thereupon, at room temperature and under stirring, into this mixture were dripped 3 g of 1,5-dichloro-1-fluoro-pent-1-ene. The mixture was stirred for 5 hours at 25° C. After washing with water, extraction with ether, drying and evaporizing, there were obtained 3 g of raw product purified by chromatography in a column (cis-, trans- isomer mixture) and which had the following characteristics:

$^1$H NMR (CDCl$_3$) δ: 1.35–2.45 (6H, multiplet), 3.65 (2H, s), 4.45–5.45 (1H, m), 7.25 (5H, s).

EXAMPLE 11

Preparation of 1-chloro-1-fluoro-7-benzylthio-hept-1-ene (our mark JH107):

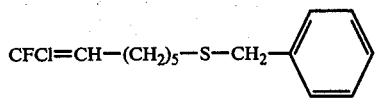

Operating as described in Example 10, from 3 g of 1,7-dichloro-1-fluoro-hept-1-ene, 2.14 g of benzylmercaptan, 0.7 g of NaH (at 55% concentration in paraffin oil) and 30 ml of N,N-dimethylformamide there were obtained 2.8 g of product which was purified in a chromatography column.

EXAMPLE 12

Synthesis of 1-(7-chloro-hept-6-inyl-oxy-)-3,4-methylendioxy-benzene (JH 109).

A — 1,7-dichlorohept-1-yn.

47 g of 1,1,7-tetrachloroheptane were additioned with 40 ml of NaOH at 50% concentration and 1 g of tetrabutylammonium iodide.

The reaction mixture was heated for 8 hours at 80°–90° C under stirring, then cooled down and extracted with ethyl ether.

The ether phase was neutralized, repeatedly washed with water, then dried and evaporated.

By distillation of the residual product there were obtained 6 g of unreacted product, 22 g of 1,1,7-trichloro-hept-1-ene (b.p. 32 55° C at 0.4 mm Hg), and 11 g of 1,7-dichloro-hept-1-yn (b.p. = 47° C at 0.4 mm Hg, IR absorption band spectrum at 2220 cm$^{-1}$).

B — 1-(7-chloro-hept-6-inyl-oxy)-3,4-methylendioxybenzene.

2.5 g of 3,4-methylendioxyphenol were dissolved in 20 ml of N,N-dimethylformamide and to this solution was added 0.8 g of NaH (50% suspension in paraffin oil). The resulting mixture was heated for 30 minutes at 50° C, after which it was cooled to room temperature and additioned with 2.5 g of 1,7-dichloro-hept-1-yn. Thereupon it was again heated to 50° C and kept at that temperature for 8 hours under stirring. The mixture was then cooled and poured into an equivalent volume of H$_2$O. The organic phase and the ether extracts of the aqueous phase were mixed together, washed with water, dried and concentrated at reduced pressure. The raw product obtained was purified by chromatography in a column on silica, using a 5% mixture of ethyl ether in hexane as eluent.

There were obtained 1.5 g of 7-chloro-hept-6-inyl-oxy-3,4-methylendioxybenzene in the form of a clear oil whose $^1$H NMR spectrum gave the following readings: δ (CDCl$_3$) = 1.4–1.9 (6H, complex), 2.2 (2H, t), 3.9 (2H, t), 5.9 (2H, s), 6.2–6.9 (3H, complex).

EXAMPLE 13

Using the procedure described in the preceding example (part B) and operating with the following phenols:
p-ethylphenol
p-methoxyphenol
p-chlorophenol
p-methylphenol
p-isopropylphenol
p-allyloxyphenol
p-propargyloxyphenol
p-methylthiophenol
p-acetylphenol
p-methoxycarbonylphenol
p-cyanophenol
p-nitrophenol
2,4-dichlorophenol the following compounds were obtained:
1-(7-chloro-hept-6-inyl-oxy)-4-ethylbenzene (JH 108)
1-(7-chloro-hept-6-inyl-oxy)-4-methoxybenzene 1-(7-chloro-hept-6-inyl-oxy)-4-chlorobenzene (JH 93)
1-(7-chloro-hept-6-inyl-oxy)-4-methylbenzene
1-(7-chloro-hept-6-inyl-oxy)-4-isopropylbenzene
1-(7-chloro-hept-6-inyl-oxy)-4-allyloxybenzene
1-(7-chloro-hept-6-inyl-oxy)-4-methylthiobenzene
1-(7-chloro-hept-6-inyl-oxy)-4-acetylbenzene
1-(7-chloro-hept-6-inyl-oxy)-4-methoxycarbonylbenzene
1-(7-chloro-hept-6-inyl-oxy)-4-cyanobenzene
1-(7-chloro-hept-6-inyl-oxy)-4-nitrobenzene
1-(7-chloro-hept-6-inyl-oxy)-2,4-dichlorobenzene.

EXAMPLE 14

Synthesis of 1-(7,7-dichloroheptyl-oxy)-3,4-methylendioxybenzene:

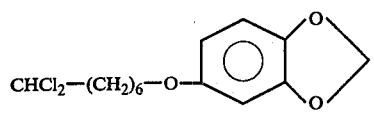

Operating as described in Example 8 (part B), from 3 g of 1,1,7-trichloro-heptane (prepared as described in Example 2), 2.1 g of 3,4-methylen-dioxyphenol, 0.4 g of NaH and 30 ml of N,N-dimethylformamide, there were obtained 4 g of product which, after purification by chromatography in a column, had a $^1$H NMR spectrum and, on elementary analysis, had values corresponding to 1-(7,7-dichloroheptyl-oxy) 3,4-methylenedioxy benzene.

EXAMPLE 15

Synthesis of 1-(7,7,7-trichloroheptyl-oxy)-3,4-methylene-dioxybenzene:

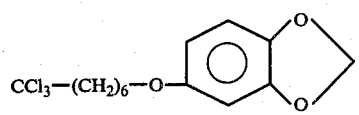

Operating as described in Example 8 (part B), from 3 g of 1,1,1,8-tetrachloroheptane (prepared as described in Example 7), 2.1 g of 3,4-methylendioxyphenol, 0.4 g of NaH and 30 ml of N,N-dimethylformamide, there were obtained 3 g of product, which when purified by chromatography in a column had the correct $^1$H NMR spectrum and gave the correct values on elementary analysis.

EXAMPLE 16

Biological activity

The tests were conducted in a conditioned environment on the following species of insects: *Tenebrio molitor, Aedes Aegipti, Tetranychus urticae*, (adults and eggs).

The conditions under which the tests were performed, as well as the evaluating criteria followed, are indicated below for each species, in the given order:

(1) *Tenebrio molitor m.* — Pupae aged 0-24 hours were treated by topical application on the last but two urosternite with an acetonic solution of the product (2 cu. mm). The results were checked after 9 days, when the insects of the witness (control) group had completed their emergence from the cocoon. As activity index there was adopted the percentual ratio of dead individuals, or misshaped and anomalous individuals with respect to the number of treated individuals, according to the formula:

$$\text{Activity} = \frac{\text{individuals (dead + misshaped + abnormal)}}{\text{treated individuals}} \%$$

(2) *Aedes Aegipti* — 3 cc of an acetone solution of the product were mixed with 297 cc of tap water into which were then transferred 25 larvae 4 days old and to which suitable nourishment was supplied. The results were taken every 2 or 3 days, until the end of the emergence of the larvae that had been kept as witnesses (controls).

The activity was assessed as in the case of Tenebrio molitor.

(3) *Tetranychus urticae*. — eggs: leaf discoids of bean plants were infested with acari eggs and subsequently treated by sprinking with an aqueous dispersion of the product under examination in a 0.1% concentration. The percentual mortality was valued 0 for the untreated foliar discs.

Adults: foliar discs of bean plant were infested with acari adults and subsequently treated with a 0.1% aqueous dispersion of the product under examination. The percentual mortality was valued 0 for the untreated foliar discs.

The results obtained are reported in the Table.

TABLE

Juvenile hormone activity and acaride activity of compounds of the invention

| Compound | Tenebrio molitor 200 γ/ins. | Aedes Aegipti 2 p.p.m. | Tetranychus urticae adults 1%°/∞ | Tetranychus urticae eggs 1%°/∞ |
|---|---|---|---|---|
| JH 88 | 100 | 100 | 96 | 100 |
| JH 89 | 70 | 82 | 53 | 100 |
| JH 92 | 100 | 100 | 100 | 97 |
| JH 93 | 100 | 100 | 98 | 100 |
| JH 107 | 100 | 100 | 100 | 100 |
| JH 108 | 100 | 100 | 100 | 100 |
| JH 109 | 100 | 100 | 99 | 100 |
| JH 96 | 100 | 100 | 100 | 100 |
| JH 97 | 100 | 69 | 44 | 100 |
| JH 98 | 97 | 8 | 73 | 86 |
| JH 99 | 100 | 100 | 100 | 100 |
| JH 100 | 100 | 100 | 93 | 100 |
| JH 101 | 100 | 100 | 100 | 100 |

We claim:

1. Phenyl or thio- ethers having both juvenile hormone and acaricide action, characterized in comprising a linear aliphatic chain with a halogenated end group and being of the general formula

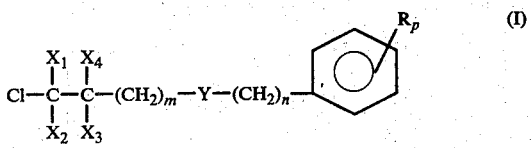

wherein:
$X_1$ = H, F, Cl, or together with $X_2$, $X_3$ and $X_4$ represents a threefold C—C bond;
$X_2$ = Cl or, when $X_1$ is different from Cl, represents, together with $X_3$ or with $X_4$, a double C═C bond; or, together with $X_1$, $X_2$ and $X_4$ represents a threefold C—C bond;
$X_3$ = H, Cl or when $X_1$ is different from Cl forms, together with $X_2$, a double C═C bond; or together with $X_1$, $X_2$ and $X_4$ forms a threefold C—C bond;

$X_4$ = H; or, when $X_1$ is different from Cl, forms, together with $X_2$, a double C—C bond; or, together with $X_1$, $X_2$ and $X_3$ forms a threefold C—C bond;

Y = O, S;

m = 3,5,7;

n = 0, 1;

p = a whole number from 1 to 4;

R = 3,4-dioxymethylene.

2. An ether according to claim 1 and which is 1-(7-chloro-hept-6-inyl-oxy)-3,4-methylendioxy benzene of the formula:

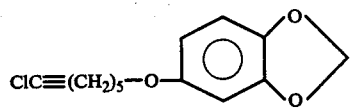

3. An ether according to claim 1, and which is 1-(7,7-dichloro-7-fluoro-heptyl-oxy)-3,4-methylendioxybenzene of the formula:

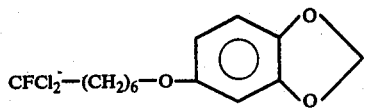

4. An ether according to claim 1, and which is 1-(7-chloro-7-fluoro-hept-6-enyl-oxy)-3,4-methylendioxybenzene of formula:

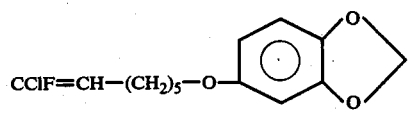

* * * * *